United States Patent
Sturgis et al.

(10) Patent No.: US 9,937,113 B2
(45) Date of Patent: *Apr. 10, 2018

(54) ANTIPERSPIRANT COMPOSITIONS

(71) Applicant: The Procter & Gamble Company, Cincinnati, OH (US)

(72) Inventors: David Arthur Sturgis, Cincinnati, OH (US); Phi Van Chu, Cincinnati, OH (US); Steven Michael Wujek, Sr., Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/638,712

(22) Filed: Jun. 30, 2017

(65) Prior Publication Data
US 2017/0296448 A1    Oct. 19, 2017

Related U.S. Application Data

(63) Continuation of application No. 14/205,872, filed on Mar. 12, 2014, now Pat. No. 9,717,930.

(60) Provisional application No. 61/777,204, filed on Mar. 12, 2013.

(51) Int. Cl.
| A61K 8/28 | (2006.01) |
| A61Q 15/00 | (2006.01) |
| A61K 8/02 | (2006.01) |
| A61K 8/34 | (2006.01) |
| A61K 8/26 | (2006.01) |
| A61K 8/58 | (2006.01) |
| A61K 8/92 | (2006.01) |
| A61K 8/31 | (2006.01) |

(52) U.S. Cl.
CPC .............. *A61K 8/28* (2013.01); *A61K 8/0229* (2013.01); *A61K 8/26* (2013.01); *A61K 8/31* (2013.01); *A61K 8/342* (2013.01); *A61K 8/345* (2013.01); *A61K 8/585* (2013.01); *A61K 8/922* (2013.01); *A61Q 15/00* (2013.01); *A61K 2800/31* (2013.01)

(58) Field of Classification Search
CPC .......... A61Q 15/00; A61Q 1/02; A61Q 17/04; A61Q 19/00; A61K 8/891; A61K 8/894; A61K 8/342; A61K 8/922; A61K 8/02; A61K 8/0229; A61K 8/49; A61K 8/58; A61K 31/165

See application file for complete search history.

(56) References Cited

U.S. PATENT DOCUMENTS

| 5,254,322 A | 10/1993 | Greczyn et al. |
| 5,254,332 A | 10/1993 | Van Flahakis et al. |
| 5,302,881 A | 4/1994 | Greczyn et al. |
| 5,354,553 A | 10/1994 | Greczyn et al. |
| 5,376,362 A | 12/1994 | Murphy et al. |
| 5,378,452 A | 1/1995 | Greczyn et al. |
| 5,389,279 A | 2/1995 | Au et al. |
| 5,419,879 A | 5/1995 | Vlahakis et al. |
| 5,443,822 A | 8/1995 | Greczyn et al. |
| 5,487,887 A | 1/1996 | Benfatto |
| 5,501,812 A | 3/1996 | Vermeer et al. |
| 5,534,246 A | 7/1996 | Herb et al. |
| 5,575,990 A | 11/1996 | Benfatto |
| 5,603,925 A | 2/1997 | Ross et al. |
| 5,650,140 A | 7/1997 | Bergmann et al. |
| 5,650,141 A | 7/1997 | Bergman et al. |
| 5,650,142 A | 7/1997 | Bergmann et al. |
| 5,650,143 A | 7/1997 | Bermann et al. |
| 5,733,534 A | 5/1998 | Swain et al. |
| 5,750,096 A | 5/1998 | Guskey |
| 5,840,286 A | 11/1998 | Gardlik et al. |
| 5,840,287 A | 11/1998 | Guskey et al. |
| 5,840,288 A | 11/1998 | Guskey et al. |
| 5,846,520 A | 12/1998 | Guskey et al. |
| 5,849,276 A | 12/1998 | Guskey et al. |
| 5,861,145 A | 1/1999 | Lucas et al. |
| 5,863,524 A | 1/1999 | Mason et al. |
| 5,928,631 A | 7/1999 | Lucas et al. |
| 5,972,319 A | 10/1999 | Linn et al. |
| 5,997,850 A | 12/1999 | Tang et al. |
| 6,071,975 A | 6/2000 | Halloran |
| 6,110,451 A | 8/2000 | Matz et al. |
| 6,171,601 B1 | 1/2001 | Gardlik et al. |
| 6,187,300 B1 | 2/2001 | Motley |

(Continued)

FOREIGN PATENT DOCUMENTS

| DE | 19821691 | 11/1999 |
| DE | 19944545 | 3/2001 |
| DE | 10057767 | 5/2002 |
| EP | 0 965 331 | 12/1999 |
| EP | 1 158 956 | 12/2001 |
| EP | 1 183 003 | 3/2002 |

(Continued)

OTHER PUBLICATIONS

PCT/US2014/024148 International Search Report, dated Oct. 9, 2014 (14 pages).

(Continued)

*Primary Examiner* — Nannette Holloman
(74) *Attorney, Agent, or Firm* — Kathleen Y. Carter

(57) ABSTRACT

A solid stick antiperspirant composition is provided. The antiperspirant composition includes aluminum zirconium tetrachlorohydrex glycine having a concentration from about 10% to about 35% by weight of the composition, an anhydrous liquid carrier, one or more structurants having a concentration from about 15% to about 25% by weight of the composition, wherein the one or more structurants comprises one or more waxes and a non-ionic exthoxylated linear alcohol having a carbon chain length from about 20 to about 40. The solid stick antiperspirant composition is a single phase.

20 Claims, No Drawings

(56) References Cited

U.S. PATENT DOCUMENTS

| | | |
|---|---|---|
| 6,277,359 B1 | 8/2001 | Raths et al. |
| 6,383,503 B1 | 5/2002 | Blackmann et al. |
| 6,387,357 B1 | 5/2002 | Chopra et al. |
| 6,436,062 B1 | 8/2002 | Iwamoto et al. |
| 6,436,382 B1 | 8/2002 | Chopra et al. |
| 6,464,991 B1 | 10/2002 | Walele et al. |
| 6,485,716 B1 | 11/2002 | Fei et al. |
| 6,500,412 B1 | 12/2002 | Johansson et al. |
| 6,503,491 B2 | 1/2003 | Guenin et al. |
| 6,511,658 B2 | 1/2003 | Mattai et al. |
| 6,534,045 B2 | 3/2003 | Mattai et al. |
| 6,605,288 B1 | 8/2003 | Okawa et al. |
| 6,608,126 B2 | 8/2003 | Ferritto et al. |
| 6,649,577 B1 | 11/2003 | Bleckmann et al. |
| 6,652,842 B2 | 11/2003 | Lucia et al. |
| 6,652,867 B1 | 11/2003 | Vincent et al. |
| 6,653,378 B2 | 11/2003 | Ferritto et al. |
| 6,703,536 B2 | 3/2004 | Roe et al. |
| 6,716,441 B1 | 4/2004 | Osborne et al. |
| 6,774,179 B2 | 8/2004 | Ferritto et al. |
| 6,787,603 B2 | 9/2004 | Johnson et al. |
| 6,790,435 B1 | 9/2004 | Ma et al. |
| 6,793,929 B2 | 9/2004 | Bleckmann et al. |
| 6,803,399 B2 | 10/2004 | Ferritto et al. |
| 6,821,934 B1 | 11/2004 | Bleckmann et al. |
| 6,835,373 B2 | 12/2004 | Kolodzik et al. |
| 6,835,374 B2 | 12/2004 | Parekh et al. |
| 6,849,251 B2 | 2/2005 | Banowski et al. |
| 6,916,465 B2 | 7/2005 | Panzer et al. |
| 6,936,242 B2 | 8/2005 | Elliott et al. |
| 6,942,871 B2 | 9/2005 | Bruning et al. |
| 6,998,424 B2 | 2/2006 | Feng et al. |
| 7,204,976 B2 | 4/2007 | Popoff et al. |
| 7,235,251 B2 | 6/2007 | Hamer et al. |
| 7,452,526 B2 | 11/2008 | Walling et al. |
| 7,799,332 B2 | 9/2010 | Moghe et al. |
| 7,867,506 B2 | 1/2011 | Moghe et al. |
| 8,187,578 B2 | 5/2012 | Wahling et al. |
| 8,343,467 B2 | 1/2013 | Woehrmann et al. |
| 8,461,258 B2 | 6/2013 | Iimura et al. |
| 8,435,955 B2 | 7/2013 | Masui et al. |
| 8,546,483 B2 | 10/2013 | Tanaka et al. |
| 2001/0012860 A1 | 8/2001 | Bleckman et al. |
| 2002/0122781 A1 | 9/2002 | Pinzon et al. |
| 2003/0040571 A1 | 2/2003 | Feng et al. |
| 2003/0082126 A9 | 5/2003 | Pinzon et al. |
| 2003/0103921 A1 | 6/2003 | Brucks et al. |
| 2003/0198653 A1 | 10/2003 | Walele et al. |
| 2004/0166083 A1 | 8/2004 | Abrutyn |
| 2004/0176464 A1 | 9/2004 | Kanatani et al. |
| 2005/0095210 A1 | 5/2005 | Mattai et al. |
| 2005/0118125 A1 | 6/2005 | Mattai et al. |
| 2005/0191257 A1 | 9/2005 | Brahms et al. |
| 2005/0227906 A1 | 10/2005 | Schudel et al. |
| 2005/0288205 A1 | 12/2005 | Walele et al. |
| 2006/0013792 A1 | 1/2006 | Fontaine et al. |
| 2006/0073110 A1 | 4/2006 | Modi |
| 2006/0210502 A1 | 9/2006 | Galante et al. |
| 2006/0280716 A1 | 12/2006 | Czech et al. |
| 2007/0003499 A1 | 1/2007 | Shen et al. |
| 2007/0009472 A1 | 1/2007 | Niebauer et al. |
| 2007/0092541 A1 | 4/2007 | Walling et al. |
| 2007/0166254 A1 | 7/2007 | Bianchi |
| 2009/0010972 A1 | 1/2009 | Modafari et al. |
| 2009/0016977 A1 | 1/2009 | Modafari et al. |
| 2009/0087396 A1 | 4/2009 | Hwang et al. |
| 2009/0123392 A1 | 5/2009 | Braun et al. |
| 2009/0253612 A1 | 10/2009 | Mushrock et al. |
| 2009/0298936 A1 | 12/2009 | Clothier et al. |
| 2010/0112017 A1 | 5/2010 | Mizutani et al. |
| 2010/0196515 A1 | 8/2010 | Kamiya et al. |
| 2012/0045493 A1 | 2/2012 | Popoff et al. |
| 2012/0135056 A1 | 5/2012 | Yarlagadda et al. |
| 2012/0205002 A1 | 8/2012 | Walling et al. |
| 2012/0321578 A1 | 12/2012 | Leuridan et al. |
| 2013/0052144 A1 | 3/2013 | Claas et al. |
| 2013/0189204 A1 | 7/2013 | Duggal et al. |
| 2013/0280409 A1 | 10/2013 | Mushrock et al. |
| 2014/0260103 A1 | 9/2014 | Sturgis et al. |
| 2014/0271515 A1 | 9/2014 | Sturgis et al. |
| 2014/0271516 A1 | 9/2014 | Sturgis et al. |

FOREIGN PATENT DOCUMENTS

| | | |
|---|---|---|
| EP | 1 195 154 | 4/2002 |
| EP | 2 314 270 | 4/2011 |
| EP | 1 776 081 B1 | 8/2011 |
| FR | 2926219 | 7/2009 |
| FR | 2954094 | 6/2011 |
| GB | 2299270 A | 10/1996 |
| JP | 05115538 | 5/1993 |
| JP | 06007415 | 1/1994 |
| JP | 0662060 | 9/1994 |
| JP | 08010314 | 1/1996 |
| JP | 09157147 | 6/1997 |
| JP | 10094591 | 4/1998 |
| JP | 10147793 | 6/1998 |
| JP | 10183172 | 7/1998 |
| JP | 11106315 | 4/1999 |
| JP | 11106330 | 4/1999 |
| JP | 11106781 | 4/1999 |
| JP | 2000186025 | 7/2000 |
| JP | 2000186026 | 7/2000 |
| JP | 2000229826 | 8/2000 |
| JP | 2000300652 | 10/2000 |
| JP | 2003335629 | 11/2000 |
| JP | 2001333968 | 12/2001 |
| JP | 2003081763 | 3/2003 |
| JP | 2003300813 | 10/2003 |
| JP | 2004049889 | 2/2004 |
| JP | 2004137227 | 5/2004 |
| JP | 2004337367 | 12/2004 |
| JP | 2005082484 | 3/2005 |
| JP | 2005145877 | 6/2005 |
| JP | 2006036981 | 2/2006 |
| JP | 2006087903 | 4/2006 |
| JP | 2006298880 | 11/2006 |
| JP | 2007044422 | 2/2007 |
| JP | 200889783 | 12/2008 |
| JP | 2009001508 | 1/2009 |
| JP | 2009120525 | 6/2009 |
| JP | 2009161474 | 7/2009 |
| JP | 2010141880 | 6/2010 |
| JP | 2011148785 | 8/2011 |
| KR | 20090107340 | 10/2009 |
| KR | 20090129849 | 12/2009 |
| WO | WO 1994/09754 A1 | 5/1994 |
| WO | WO 1996/24326 A1 | 8/1996 |
| WO | WO 1996/37184 A1 | 11/1996 |
| WO | WO 1998/55088 A1 | 12/1998 |
| WO | WO 2000/67713 A1 | 11/2000 |
| WO | WO 2001/13871 A1 | 3/2001 |
| WO | WO 2001/15659 A2 | 3/2001 |
| WO | WO 2003/53388 | 7/2003 |
| WO | WO 2003/072610 | 9/2003 |
| WO | WO 2004/050045 A1 | 6/2004 |
| WO | WO 2005/099661 A1 | 10/2005 |
| WO | WO 2007/114329 | 10/2007 |
| WO | WO 2007/099738 | 9/2009 |
| WO | WO 2009/138150 | 11/2009 |

OTHER PUBLICATIONS

PCT US2014/024166 International Search Report, dated Oct. 9, 2014 (13 pages).
PCT/US2014/024337 International Search Report, dated Oct. 13, 2014 (13 pages).
Flick, Cosmetic Additives, 1991, Noyes Publiations, p. 18.
Laden, Antiperspirants and Deodorants, Second Ediition, 1999, pp. 140-141.

ANTIPERSPIRANT COMPOSITIONS

CROSS REFERENCE TO RELATED APPLICATION

This application is a continuation of application Ser. No. 14/205,872, filed Mar. 12, 2014, which claims the benefit of U.S. Provisional Application No. 61/777,204, filed Mar. 12, 2013, the substances of which are incorporated herein by reference.

FIELD OF THE INVENTION

The present disclosure generally relates to antiperspirant compositions which comprise a surfactant.

BACKGROUND OF THE INVENTION

Antiperspirant compositions have become a staple in the personal hygiene routine for many people. Various antiperspirant compositions and methods of making are known in the art. Some examples are described in U.S. Pat. Nos. 5,417,964; 5,490,979; 5,603,925; 5,733,534; 5,833,964; 5,972,319; 6,338,840; 6,752,982; 6,682,749; 7,452,526; 8,187,578; 2007/0092541; 2009/0269292 and WO 02/053109. These compositions, unlike deodorants, have the added benefit of helping to combat wetness. While wetness is generally harmless, there are social stigmas associated with underarm sweat and feelings of uncleanliness. There is, however, room for improvement with respect to the effectiveness of antiperspirant compositions to combat wetness.

SUMMARY OF THE INVENTION

In one aspect, a solid stick antiperspirant composition is provided. The antiperspirant composition includes aluminum zirconium tetrachlorohydrex glycine having a concentration from about 10% to about 35% by weight of the composition, an anhydrous liquid carrier, one or more structurants having a concentration from about 15% to about 25% by weight of the composition, wherein the one or more structurants comprises one or more waxes and a non-ionic exthoxylated linear alcohol having a carbon chain length from about 20 to about 40. The solid stick antiperspirant composition is a single phase.

In another aspect, a solid stick antiperspirant composition is provided. The antiperspirant composition includes an antiperspirant active comprising a zirconium containing salt and having a concentration from about 10% to about 35% by weight of the composition, one or more anhydrous liquid carriers, one or more structurants having a concentration from about 15% to about 25% by weight of the composition, wherein the one or more structurants comprises one or more waxes and a non-ionic exthoxylated linear alcohol. The antiperspirant composition has a Red Dot Color Value of 0.5 or less at 2, 3, 4, 5, 10 and 15 minutes and a Red Dot Color Value greater than 1 at 30 seconds and a Red Dot Color Value of 1.25 or more at 24 hours.

In yet another aspect, a solid stick antiperspirant composition is provided. The antiperspirant composition includes an antiperspirant active comprising a zirconium containing salt and having a concentration from about 10% to about 35% by weight of the composition, one or more anhydrous liquid carriers, one or more structurants having a concentration from about 15% to about 25% by weight of the composition, wherein the one or more structurants comprises one or more waxes, and a non-ionic exthoxylated linear alcohol having a carbon chain length from about 20 to about 40 and an HLB value between about 6 and about 12. The solid stick antiperspirant composition is a single phase.

DETAILED DESCRIPTION OF THE INVENTION

I. Definitions

As used herein, the following terms shall have the meaning specified thereafter:

"Ambient" refers to surrounding conditions at about one atmosphere of pressure, 50% relative humidity and about 25° C.

"Anhydrous" refers to compositions and/or components which are substantially free of added or free water.

"Antiperspirant composition" refers to antiperspirant compositions, deodorant compositions, and the like. For example, antiperspirant creams, gels, and soft solid sticks.

"Onset of crystallization" means the temperature at which a material crystallizes from a liquid solution. All melt points and the onset of crystallization referenced herein, unless otherwise specified, are measured by the well known technique of Differential Scanning calorimetry (DSC). For evaluation a Perkin-Elmer 7 Series Thermal Analysis System Model DSC7 is used, manufactured by Perkin-Elmer, Norwalk, Conn.

"Soft solid" refers to a composition with a static yield stress of about 200 Pa to about 1,500 Pa after dispensing.

"Substantially free of" refers to about 2% or less, about 1% or less, or about 0.1% or less of a stated ingredient. "Free of" refers to no detectable amount of the stated ingredient or thing.

II. Efficacy Enhancement

Solids and soft solids are two of the more popular forms of antiperspirants. However, structurants, like waxes, are used in both of these forms to help give them their structure and stability. The downside to the use of these types of structurants is that they have a tendency to interfere with the release of the active from the composition and thus negatively impact the efficacy of the product. This issue is compounded in the invisible solid form which tends to have 3-4 times more structurant than soft solids.

While reductions in structurant level could be used to help increase antiperspirant efficacy, this comes with its own challenges. Reducing the structurant level, for example, can negatively impact the stability of the product. As such, the desired solution was to find something that could be added to these types of solid products that would enhance water transport through the product film without negatively impacting stability of the product. Additionally, since soft solid product forms are generally more efficacious due to the much lower amount of structurant, a commercial soft solid product was utilized as the control.

The initial work focused on the addition of surfactants to the formulations to try and help break-up the structurant and allow for better water transport. This first attempt was unsuccessful. As can be seen in the chart below, when a current market solid (Current Solid Market Formulation 1) was tested against a solid which included a surfactant (Comparative Solid Formulation A), Comparative Solid Formulation A performed a little worse than the Current Solid Market Formulation 1 in the amount of sweat measured versus the control (a current market soft solid). When looking at the results, the less sweat the more efficacious the product.

| PRODUCT | SURACTANT | RESULT |
| --- | --- | --- |
| Comparative Solid Formulation A | Yes | 36 mg more sweat than control |
| Current Market Solid Formulation 1 | No | 33.5 mg more sweat than control |

While the initial try was a failure, it wasn't a total surprise as surfactants are sometimes used in these types of solid antiperspirants in similar levels as wash off aids. However, the current inventors believed the use of surfactants in these types of formulations could improve the efficacy so they looked to better understand what was happening chemically to the surfactants in the products. One area that was investigated was how these types of products are made.

Often, solid antiperspirant forms are made in a single batch process. This process generally involves adding all of the raw materials (except active and perfume) to a mix tank, heating it to a temperature to melt the structurants and other higher melt point ingredients, and holding it at that temperature until the appropriate ingredients are melted. This heating step can involve temperatures of, for example, 80° C. or more, and it can take from 45 minutes to an hour for the ingredients to melt. At this point, the batch is cooled to 70-75° C. and the active and perfume are added to the tank. The composition is usually mixed here for at least 15 minutes before it is cooled to 50-55° C. and poured into canisters.

There are, however, some current commercial solid antiperspirant products which utilize a split stream method of manufacturing. In the split stream method, there is generally a hot process stream and a cold process stream. The hot process stream generally involves mixing a solvent and structurant that are heated to a first temperature that is above the onset of crystallization of the hot process stream. The cold process stream generally involves mixing a solvent, an antiperspirant active, and any heat sensitive ingredients at a temperature at least about 10° C. below the onset of crystallization of the structurant in the hot stream. The two streams are then combined in such a way as to cause substantially complete mixing and heat transfer in a very short time period. This time period is usually less than 3 seconds.

Since Comparative Solid Formulation A was made with the batch process, two additional solid formulations were made with the split stream process (Inventive Example 1 and Inventive Example 2). As can be seen from the chart below, the two split stream examples with surfactant (Inventive examples 1 and 2) performed significantly better than both Comparative Solid Formulation A (with surfactant but made in a batch process) and Commercial Solid Formulation 1 (without surfactant but made in a split stream process).

| PRODUCT | SURFACTANT | PROCESS | RESULT |
| --- | --- | --- | --- |
| Soft Solid Market - CONTROL | No | Batch | control |
| Comparative Solid Formulation A | Yes | Batch | 36 mg more sweat than control |
| Commercial Solid Formulation 1 | No | Split Stream | 33.5 mg more sweat than control |
| Inventive Solid Example 1 | Yes | Split Stream | 22 mg more sweat than control |
| Inventive Solid Example 2 | Yes | Split Stream | 28.5 mg less sweat than the control |

Thus, utilizing the split stream method in combination with the surfactant positively impacted the efficacy of the product. Without intending to be limited by theory, it is believed that the surfactant likes to bind the antiperspirant active. Thus, in a single batch process where all of the ingredients are combined and mixed together for a significant amount of time, the surfactant has time to find and bind to the active which impedes its release. Conversely, in the split stream method, the surfactant is in the hot stream with the structurant and only briefly mixes with the antiperspirant containing cold stream. The product starts to crystallize shortly thereafter all of which prevents the surfactant from having much access to the active and thus less of an ability to bind to it.

So, it is believed the amount of time the surfactant and active have to interact impacts their ability to bind and impacts the resulting efficacy of the product. Thus, it is believed that if the contact time between the surfactant and active before onset of crystallization can be limited to 5 minutes or less, binding of the active by the surfactant is minimized and the resulting product will have an improved efficacy over its non-surfactant containing counterpart. Further minimizing the contact time to 3 minutes or less; 1 minute or less; 30 seconds or less; 15 seconds or less; 5 seconds or less; or 3 seconds or less are also desirable.

Moreover, Inventive Example 2 was significantly more efficacious than the soft solid control. This is very surprising given the differences in structurant level between the two forms. The only difference between Inventive Examples 1 and 2 is the type of active. Inventive Formula 1 utilized aluminum zirconium trichlorohydrex while Inventive Formula 2 utilized aluminum zirconium tetrachlorohydrex. While aluminum zirconium tetrachlorohydrex actives are more acidic and can potentially provide an incremental efficacy boost, it is surprising to see this much of an additional boost in efficacy.

Another way to look at efficacy enhancement is with the Red Dot method. This method looks at how water is transported into and then released from the product film. So, for the biggest impact, there is a balance between how quickly water can get into the product and how well it gets out. This is important because the effectiveness of an antiperspirant is related to the transport of sweat (water) in and out of the product film to solubilize the active and transport it back into the sweat duct to form a plug.

Anything that can impede transport can reduce the efficacy of the product. For example, the Indicator solution would have a high a-value by itself without being neutralized by any acidic salts. A highly efficacious product would have a relatively high a-value (greater than 1.0) after 30 seconds. This demonstrates that the product film is not too hydrophilic, so that it does not immediately start interacting with the acidic pH of the active within the product film. A lower value (below 1.0) indicates the product film is very hydrophilic, which like a large diameter (discussed below), can impede transport out of the product film and reduce efficacy.

To ensure proper transport through the product film, it is also desirable to see the a-value decrease significantly (below an a-value of 0.6) between 2 and 15 minutes. This shows that the product film is capable of transporting the indicator efficiently to the active to be neutralized by the acidity of the active. This is important because this indicates efficient transport into the product film to solubilize the active. At this time point, the higher the a-value the less efficient the product film is at transporting moisture to the active.

After 24 hours, it is desirable to see the a-value increase back above 1.0 or more. A reading below this value suggests the now acidic solution was not able to transport out of the product film efficiently leaving some active trapped in the product film and reducing the efficiency of transport during the next sweat event. Since a consumer may undergo multiple sweat events during the course of usage, it is desirable to ensure the product film is efficient for transport during multiple sweat events, not just the first. Some Red Dot measurements for some current market invisible solid (IS) formulations and an inventive formulation are below.

Comparing Current Inventive Formula IS #2 to the two closest Current Market Products from a Red Dot Method measurement point of view, Current Market IS #2 has such a low a-value after 30 seconds and such a large diameter that it suggests this product film is very hydrophilic and that will negatively impact efficacy by impeding transport out of the product film. And Current Market IS #6 has a 24 hour average that is too low, which shows the product film will not be efficient through multiple sweat events, resulting in lower efficacy due to the fact that a significant amount of the active was not able to transport out of the product film, significantly reducing efficacy.

Another way to look at the results from the Red Dot Method is to measure the diameter of the spot created during the test. The diameter of the spot can show the interaction between sweat (indicator) and the product film. Since the amount of indicator applied is controlled and constant, the diameter is an indirect measure of contact angle. Too small of a diameter indicates the product film is much too hydrophobic, resulting in a large contact angle and small diameter. This indicates water will have a hard time transporting into the product film, reducing efficacy. If the diameter is too large, it suggests the product film itself is too hydrophilic resulting in a low contact angle. A product film that is very hydrophilic may have high transport into the film, but low transport out of the film. Therefore, the ideal contact angle and diameter is one that is not too large and not too small. This will have the proper balance of maximizing transport into the product film without hurting transport our of the product film. Thus, a desirable diameter is from about 2.0 cm to about 3.5 cm.

| Current Market IS #2 | Current Market IS #3 | Current Market IS #4 | Current Market IS #5 | Current Market IS #6 | Current Market IS #7 | Inventive Solid Example #2 | Current Market IS #8 | Current Market IS #9 |
|---|---|---|---|---|---|---|---|---|
| 4.06 | 1.97 | 2.81 | 2.19 | 2.79 | 2.20 | 2.89 | 3.05 | 2.14 |

The importance of the Red Dot Test in predicting better water properties is likewise true in soft solid forms. As can be seen in the chart below, Market SS #1-#4 all have a significantly higher a-value (above 0.5) between 2 and 15 mins, this shows that the transport into the product film is not efficient and will result in significantly reduced efficacy.

| Time | Current Market SS #1 | Current Market SS #2 | Current Market SS #3 | Current Market SS #4 | Inventive Soft Solid Formula #1 |
|---|---|---|---|---|---|
| 30 s avg | 1.61 | 2.14 | 2.16 | 2.28 | 1.89 |
| 1 min avg | 1.31 | 1.62 | 1.95 | 1.97 | 0.48 |
| 2 min avg | 0.99 | 1.47 | 1.93 | 1.36 | −0.13 |
| 3 min avg | 0.74 | 1.31 | 1.85 | 1.03 | −0.10 |
| 4 min avg | 0.63 | 1.12 | 1.65 | 0.73 | −0.13 |
| 5 min avg | 0.59 | 1.08 | 1.41 | 0.64 | −0.26 |
| 10 min avg | 0.79 | 1.20 | 1.49 | 0.86 | −0.31 |

| Time | Current Market IS #2 | Current Market IS #3 | Current Market IS #4 | Current Market IS #5 | Current Market IS #6 | Current Market IS #7 | Inventive Solid Example #2 | Current Market IS #8 | Current Market IS #9 |
|---|---|---|---|---|---|---|---|---|---|
| 30 s avg | −0.28 | 2.61 | −0.37 | 1.75 | 1.79 | 2.77 | 1.80 | 1.62 | 2.10 |
| 2 min avg | −0.74 | 1.38 | −0.52 | 0.50 | 0.32 | 1.70 | 0.31 | 0.55 | 0.73 |
| 3 min avg | −0.87 | 1.02 | −0.38 | 0.32 | 0.14 | 1.45 | 0.28 | 0.70 | 0.59 |
| 4 min avg | −0.81 | 0.89 | −0.47 | 0.46 | 0.25 | 1.26 | 0.32 | 0.74 | 0.51 |
| 5 min avg | −0.75 | 0.96 | −0.62 | 0.47 | 0.18 | 1.09 | 0.23 | 0.68 | 0.58 |
| 10 min avg | −0.69 | 1.08 | −0.57 | 0.42 | 0.20 | 1.23 | 0.11 | 0.74 | 0.71 |
| 15 min avg | −0.66 | 0.96 | −0.56 | 0.57 | 0.07 | 1.24 | 0.18 | 0.74 | 0.64 |
| 2-15 min avg | −0.76 | 1.00 | −0.52 | 0.45 | 0.17 | 1.27 | 0.23 | 0.72 | 0.61 |
| 24 hr avg | 1.72 | 1.78 | 1.19 | 1.94 | 0.79 | 3.21 | 1.67 | 1.66 | 1.32 |

-continued

| Time | Current Market SS # 1 | Current Market SS # 2 | Current Market SS # 3 | Current Market SS # 4 | Inventive Soft Solid Formula # 1 |
|---|---|---|---|---|---|
| 15 min avg | 0.82 | 1.24 | 1.50 | 0.86 | −0.44 |
| 2-15 min avg | 0.76 | 1.24 | 1.64 | 0.91 | −0.23 |
| 24 hr avg | 1.83 | 1.66 | 1.57 | 1.02 | 0.92 |

Likewise, the average diameter from the Red Dot Method is also helpful in predicting more efficacious soft solid forms. See the chart below. Market SS #1-#4 all have relatively low diameters (below 2.5) indicating the product films are very hydrophobic, suggesting inefficient transport through the product film and lower efficacy.

| Current Market SS # 1 | Current Market SS # 2 | Current Market SS # 3 | Current Market SS # 4 | Inventive Soft Solid Formula # 1 |
|---|---|---|---|---|
| 1.90 | 1.62 | 1.62 | 2.04 | 3.10 |

III. Antiperspirant Compositions

Antiperspirant compositions as described herein will contain an antiperspirant active, a structurant, and a surfactant. The compositions may also comprise an anhydrous liquid carrier and other components as described below. The antiperspirant compositions are a single phase meaning the final product is homogenous, and all of the liquids are in the same continuous phase. They are not macroscopically separated by a physical separation into distinct regions of 3D space which could allow for some heterogeneity across the product. The liquids also do not contain a dispersed phase, microscopically separated such as in an emulsion (water in oil or oil in water). Solid antiperspirant compositions can be in solid form, like a stick for example, or a less rigid form, like a soft solid for example. Soft solids generally have a hardness of about 400 gram force or less after dispensing, while solids generally have a hardness of about 600 gram force or more before dispensing. Hardness can be measured in accordance with the Product Hardness method described below.

Antiperspirant Active

Solid antiperspirant compositions may comprise an antiperspirant active suitable for application to human skin. The concentration of the antiperspirant active in the composition should be sufficient to provide the desired enhanced wetness protection. For example, the active may be present in an amount of from about 0.1%, about 0.5%, about 1%, about 5%, or about 10%; to about 60%, about 35%, about 25% or about 20%, by weight of the composition. These weight percentages are calculated on an anhydrous metal salt basis exclusive of water and any complexing agents such as glycine, glycine salts, or other complexing agents.

An antiperspirant active can include any compound, composition, or other material having antiperspirant activity. Such actives may include astringent metallic salts, especially inorganic and organic salts of aluminum, zirconium and zinc, as well as mixtures thereof. For example, the antiperspirant actives may include zirconium-containing salts or materials, such as zirconyl oxyhalides, zirconyl hydroxyhalides, and mixtures thereof and/or aluminum-containing salts such as, for example, aluminum halides, aluminum chlorohydrate, aluminum hydroxyhalides, and mixtures thereof.

1. Aluminum Salts

Aluminum salts useful herein can include those that conform to the formula:

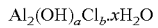

$$Al_2(OH)_aCl_b \cdot xH_2O$$

wherein a is from about 2 to about 5; the sum of a and b is about 6; x is from about 1 to about 6; where a, b, and x may have non-integer values. For example, aluminum chlorohydroxides referred to as "5/6 basic chlorohydroxide," wherein a is about 5 and "2/3 basic chlorohydroxide", wherein a=4 may be used.

A general description of these aluminum salts can be found in *Antiperspirants and Deodorants*, Cosmetic Science and Technology Series Vol. 20, $2^{nd}$ edition, edited by Karl Laden. Mixtures of aluminum salts are described in British Patent Specification 1,347,950, filed in the name of Shin et al. and published Feb. 24, 1974.

2. Zirconium Salts

Zirconium salts useful herein can include those which conform to the formula:

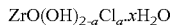

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, issued to Schmitz on Aug. 4, 1975. Useful to the present invention are zirconium salt complexes that additionally contain aluminum and glycine, commonly known as "ZAG complexes". These complexes can contain aluminum chlorohydroxide and zirconyl hydroxy chloride conforming to the above-described formulas. Examples of two such complexes include aluminum zirconium trichlorohydrex and aluminum zirconium tetrachlorohydrex.

Structurants

Antiperspirant compositions can also comprise a structurant to help provide the composition with the desired viscosity, rheology, texture and/or product hardness, or to otherwise help suspend any dispersed solids or liquids within the composition. The term "structurant" may include any material known or otherwise effective in providing suspending, gelling, viscosifying, solidifying, or thickening properties to the composition or which otherwise provide structure to the final product form. These structurants may include, for example, gelling agents, polymeric or nonpolymeric agents, inorganic thickening agents, or viscosifying agents. The thickening agents may include, for example, organic solids, silicone solids, crystalline or other gellants, inorganic particulates such as clays or silicas, or combinations thereof.

The concentration and type of the structurant selected for use in the antiperspirant composition will vary depending upon the desired product form, viscosity, and hardness. The thickening agents suitable for use herein, may have a concentration range from about 0.1%, about 2%, about 3%, about 5%; or about 10%; to about 35%, about 20%, about 10%, or about 8%, by weight of the composition. Soft solids will often contain a lower amount of structurant than solid compositions. For example, a soft solid may contain from about 1.0% to about 9%, by weight of the composition, while a solid composition may contain from about 15% to about 25%, by weight of the composition, of structurant. This is not a hard and fast rule, however, as a soft solid product with a higher structurant value can be formed by, for example, shearing the product as it is dispensed from a package.

Non-limiting examples of suitable gelling agents include fatty acid gellants, salts of fatty acids, hydroxyl acids, hydroxyl acid gellants, esters and amides of fatty acid or hydroxyl fatty acid gellants, cholesterolic materials, dibenzylidene alditols, lanolinolic materials, fatty alcohols, triglycerides, sucrose esters such as SEFA behenate, inorganic materials such as clays or silicas, other amide or polyamide gellants, and mixtures thereof.

Suitable gelling agents include fatty acid gellants such as fatty acid and hydroxyl or alpha hydroxyl fatty acids, having from about 10 to about 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred gelling agents are 12-hydroxystearic acid, esters of 12-hydroxystearic acid, amides of 12-hydroxystearic acid and combinations thereof.

Other suitable gelling agents include amide gellants such as di-substituted or branched monoamide gellants, mono-substituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816, issued Jul. 4, 1995, and U.S. Pat. No. 5,840,287, filed Dec. 20, 1996.

Still other examples of suitable gelling agents include fatty alcohols having at least about 8 carbon atoms, at least about 12 carbon atoms but no more than about 40 carbon atoms, no more than about 30 carbon atoms, or no more than about 18 carbon atoms. For example, fatty alcohols include but are not limited to cetyl alcohol, myristyl alcohol, stearyl alcohol and combinations thereof.

Non limiting examples of suitable triglyceride gellants include tristearin, hydrogenated vegetable oil, trihydroxysterin (Thixcin® R, available from Rheox, Inc.), rape seed oil, castor wax, fish oils, tripalmitin, Syncrowax® HRC and Syncrowax® HGL-C(Syncrowax® available from Croda, Inc.).

Other suitable thickening agents include waxes or wax-like materials having a melt point of above 65° C., more typically from about 65° C. to about 130° C., examples of which include, but are not limited to, waxes such as beeswax, carnauba, bayberry, candelilla, montan, ozokerite, ceresin, hydrogenated castor oil (castor wax), synthetic waxes and microcrystalline waxes. Castor wax is preferred within this group. The synthetic wax may be, for example, a polyethylene, a polymethylene, or a combination thereof. Some suitable polymethylenes may have a melting point from about 65° C. to about 75° C. Examples of suitable polyethylenes include those with a melting point from about 60° C. to about 95° C. Other high melting point waxes are described in U.S. Pat. No. 4,049,792, Elsnau, issued Sep. 20, 1977.

Further structurants for use in the solid antiperspirant compositions of the present invention may include inorganic particulate thickening agents such as clays and colloidal pyrogenic silica pigments. For example, colloidal pyrogenic silica pigments such as Cab-O-Sil®, a submicroscopic particulated pyrogenic silica may be used. Other known or otherwise effective inorganic particulate thickening agents that are commonly used in the art can also be used in the solid antiperspirant compositions of the present invention. Concentrations of particulate thickening agents may range, for example, from about 0.1%, about 1%, or about 5%; to about 35%, about 15%, about 10% or about 8%, by weight of the composition.

Suitable clay structurants include montmorillonite clays, examples of which include bentonites, hectorites, and colloidal magnesium aluminum silicates. These and other suitable clays may be hydrophobically treated, and when so treated will generally be used in combination with a clay activator. Non-limiting examples of suitable clay activators include propylene carbonate, ethanol, and combinations thereof. When clay activators are present, the amount of clay activator will typically range from about 40%, about 25%, or about 15%; to about 75%, about 60%, or about 50%, by weight of the clay.

Surfactant

Solid antiperspirant compositions comprise a surfactant. A surfactant is generally present at a level of about 0.05% to about 5%, by weight of the composition, but may contain, from about 0.5% to about 5%, from about 1.0% to about 4%; from about 1.5% to about 3.5%; from about 1.75% to about 2.5%; about 2%, or any combination thereof. The surfactant can have a HLB range of about 2 to about 14; about 6 to about 12; about 8 to about 10; or any combination thereof. The surfactant may be free of polyoxyethylene sorbitan fatty acids. The surfactant may comprise, for example, a $C_{20-40}$ Pareth-10. Another suitable surfactant is a nonionic exthoxylated linear alcohol with a carbon chain length of 20-40. One specific example of a suitable surfactant includes PERFORMATHOX™ 450 ethoxylate.

Anhydrous Liquid Carrier

Solid antiperspirant compositions may further comprise anhydrous liquid carriers. These are present, for example, at concentrations ranging from about 10%, about 15%, about 20%, about 25%; to about 99%, about 70%, about 60%, or about 50%, by weight of the composition. Such concentrations will vary depending upon variables such as product form, desired product hardness, and selection of other ingredients in the composition. The anhydrous carrier may be any anhydrous carrier known for use in personal care applications or otherwise suitable for topical application to the skin. For example, anhydrous carriers may include, but are not limited to volatile and nonvolatile fluids.

A. Volatile Fluid

An antiperspirant composition may further comprise a volatile fluid such as a volatile silicone carrier. Volatile fluids are present, for example, at concentrations ranging from about 20% or from about 30%; to about 80%, or no about 60%, by weight of the composition. The volatile silicone of the solvent may be cyclic, linear, and/or branched chain silicone. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976).

The volatile silicone may be a cyclic silicone. The cyclic silicone may have from about 3 silicone atoms, or from about 5 silicone atoms; to about 7 silicone atoms, or about 6 silicone atoms. For example, volatile silicones may be used which conform to the formula:

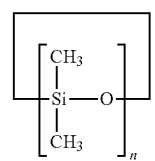

wherein n is from about 3, or from about 5; to about 7, or about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof.

B. Non-Volatile Fluid

An antiperspirant composition may further comprise a non-volatile fluid. These non-volatile fluids may be either non-volatile organic fluids or non-volatile silicone fluids.

1. Non-Volatile Organic Fluids

The non-volatile organic fluid can be present, for example, at concentrations ranging from about 1%, from about 2%; to about 20%, or about 15%, by weight of the composition.

Non-limiting examples of nonvolatile organic fluids include, but are not limited to, mineral oil, PPG-14 butyl ether, isopropyl myristate, petrolatum, butyl stearate, cetyl octanoate, butyl myristate, myristyl myristate, C12-15 alkylbenzoate (e.g., Finsolv™), dipropylene glycol dibenzoate, PPG-15 stearyl ether benzoate and blends thereof (e.g. Finsolv TPP), neopentyl glycol diheptanoate (e.g. Lexfeel 7 supplied by Inolex), octyldodecanol, isostearyl isostearate, octododecyl benzoate, isostearyl lactate, isostearyl palmitate, isononyl/isononoate, isoeicosane, octyldodecyl neopentanate, hydrogenated polyisobutane, and isobutyl stearate. Many such other carrier liquids are disclosed in U.S. Pat. No. 6,013,248 (Luebbe et al.) and U.S. Pat. No. 5,968,489 (Swaile et al).

2. Nonvolatile Silicone Fluids

An antiperspirant composition may further comprise a non-volatile silicone fluid. The non-volatile silicone fluid may be a liquid at or below human skin temperature, or otherwise in liquid form within the anhydrous antiperspirant composition during or shortly after topical application. The concentration of the non-volatile silicone may be from about 1%, from about 2%; to about 15%, about 10%, by weight of the composition. Nonvolatile silicone fluids of the present invention may include those which conform to the formula:

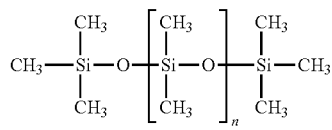

wherein n is greater than or equal to 1. These linear silicone materials may generally have viscosity values of from about 5 centistokes, from about 10 centistokes; to about 100,000 centistokes, about 500 centistokes, about 200 centistokes, or about 50 centistokes, as measured under ambient conditions.

Specific non limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18(350) Silicone Fluids (available from G.E. Silicones).

Low surface tension non-volatile solvent may be also be used. Such solvents may be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Malodor Reducing Agent

An antiperspirant composition may comprise a malodor reducing agent. Malodor reducing agents include components other than the antiperspirant active within the composition that act to eliminate the effect that body odor has on fragrance display. These agents may combine with the offensive body odor so that they are not detectable including, but not limited to, suppressing evaporation of malodor from the body, absorbing sweat or malodor, masking the malodor or microbiological activity on odor causing organisms. The concentration of the malodor reducing agent within the composition is sufficient to provide such chemical or biological means for reducing or eliminating body odor. Although the concentration will vary depending on the agent used, generally, the malodor reducing agent may be included within the composition from about 0.05%, about 0.5%, or about 1%; to about 15%, about 10%, or about 6%, by weight of the composition.

Malodor reducing agents of the present invention may include, but are not limited to, pantothenic acid and its derivatives, petrolatum, menthyl acetate, uncomplexed cyclodextrins and derivatives thereof, talc, silica and mixtures thereof. Such agents may be used as described in U.S. Pat. No. 6,495,149, issued to Scavone, et al and US patent application 2003/0152539, filed Jan. 25, 2002 in the names of Scavone, et al.

For example, if panthenyl triacetate is used, the concentration of the malodor reducing agent may be from about 0.1% or about 0.25%; to about 3.0%, or about 2.0%, by weight of the composition. Another example of a malodor reducing agent is petrolatum which may be included from about 0.10%, or about 0.5%; to about 15%, or about 10%, by weight of the composition. A combination may also be used as the malodor reducing agent including, but not limited to, panthenyl triacetate and petrolatum at levels from about 0.1%, or 0.5%; to about 3.0%, or about 10%, by weight of the composition. Menthyl acetate, a derivative of menthol that does not have a cooling effect, may be included from about 0.05%, or 0.01%; to about 2.0%, or about 1.0%, by weight of the composition. The malodor reducing agent of the present invention may be in the form of a liquid or a semi-solid such that it does not contribute to product residue.

Red Dot Values

Antiperspirant compositions as discussed herein will have color a-values as measured according to the Red Dot Method below. Red dot a-value measurements are generally taken at 30 seconds; 2 minutes; 3 minutes; 4 minutes; 5 minutes; 10 minutes; 15 minutes; and 24 hours. A color a-value at 30 seconds can be, for example, from about 1, about 1.25, or from about 1.5; to about 3.0; or about 4.0. A color a-value at time points 2 minutes; 3 minutes; 4 minutes; 5 minutes; 10 minutes; and 15 minutes can be, for example, 0.5 or less at each time point. Additionally, the a-values at each of time points 2 minutes; 3 minutes; 4 minutes; 5 minutes; 10 minutes; and 15 minutes can be averaged and then the value can be, for example, about 0.50 or less or about 0.40 or less. A color a-value at 24 hours can be, for example, about 0.75 or more; about 1.0 or more; about 1.25 or more; or about 1.5 or more; to about 3.0 or less; or about 4.0 or less. A 24 diameter reading can be, for example, from about 2.25; or about 2.5; to about 3.5; or about 3.25.

IV. Methods of Use

The compositions as described above also give rise to some useful methods. For example, one method includes method of enhancing efficacy in a solid antiperspirant composition comprising combining about 10% to about 20%, by weight of the composition, of an antiperspirant active, a structurant, and a surfactant, wherein the composition has a hardness of about 600 gram force or more prior to dispensing and has a Red Dot color a-value greater than 1 at 30 seconds and a 24 hour color a-value of 1.25 or more. Another useful method includes a method of enhancing efficacy in a solid antiperspirant composition comprising combining about 2% to about 8%, by weight of the composition, of an antiperspirant active, a structurant, and a surfactant, wherein the composition has a hardness of about 400 gram force or less after dispensing and has a Red Dot color a-value of 0.50 or less at the values of 2, 3, 4, 5, 10, and 15 minutes. All of the specifics of the compositions and their properties discussed above may be used herein in the methods.

V. Methods of Manufacturing

Any method of manufacturing which minimizes the contact of an antiperspirant active and a surfactant can be used. However, one specific method of manufacturing includes a split stream method. This method is described in more detail above.

VI. Test Methods

Static Yield Stress/High Shear Viscosity

To determine static stress yield values for the antiperspirant soft solid compositions herein, a two-part test can be conducted. First, a controlled stress ramp can ramp up linearly, and can measure a shear rate at each point of stress. In the second part of the two-part test, a controlled shear rate ramp can be linearly increased and shear stress can be measured. A rheological model can be used to fit the data in both segments of the test, and a value can be determined from the rheological model for both segments.

Compositions are collected after they have been dispensed through their consumer use package and can be analyzed using a rheometer. In particular, the rheometer can be a Thermo Scientific Haake RheoStress 600 (available from TA Instruments, New Castle, Del., U.S.A.) and data collection and analysis can be performed using rheology software, which can be RheoWin Software Version 2.84 or greater.

To prepare product samples, each product sample can be conditioned at about 23° C. until rheological properties can stabilize. An incubation period can be specified for each type of antiperspirant soft solid composition.

To operate the rheometer, parallel plates can be installed, and using the rheology software, a zero point for a gap between the parallel plates can be determined. A sufficient amount of the product sample can be loaded to ensure that entire serrated portions of the parallel plates can be in contact with the product sample once the product sample can be in a measurement position. A spatula can be used to carefully scrape dispensed product onto the serrated portion of a base plate. Once the product can be loaded, the rheology software can be used to move the parallel plates. A controlled stress ramp can be conducted followed by a controlled shear rate ramp.

Next, the rheology software can be used to determine shear yield stress values based on the controlled stress ramp and the controlled shear rate ramp. Data from the rheology test can be plotted as viscosity (Pa-s) on a log scale versus linear applied stress (Pa). "Static yield stress" refers to a point in a stress sweep analysis of a product at which point the rheometer is first capable of measuring product viscosity. The static yield stress is extrapolated from the data from a flow region along a shear rate measurement within 50-5001/s.

Red Dot Method

A. Preparation of Starting Solutions:

A Phenol Red/Deionized Water solution (Deionized Water, 99.985% per weight; Phenol Red, 0.015% per weight) can be prepared as follows: Add Phenol Red powder to deionized water at room temperature based on the percentages noted. Stir for approximately 2 minutes at approximately 500 rpm, or until the powdered phenol red is completely dissolved into solution, using a magnetic stir bar and stir plate.

A Potassium Hydroxide/Deionized Water solution (Deionized Water, 95% per weight; Potassium Hydroxide (solid), 5% per weight) can be prepared as follows: Add Potassium Hydroxide pellets to deionized water at room temperature based on the noted percentages. Stir for approximately 1 minute at approximately 500 rpm, or until the potassium hydroxide is completely dissolved into solution, using a magnetic stir bar and stir plate.

B. Preparation of pH-Indicator Solution:

The pH-indicator solution can be prepared as follows: Weigh 200 grams of above Phenol Red/Deionized Water solution into a glass beaker. At ambient conditions, stir solution continuously at 100 rpm using a magnetic stir bar and stir plate. Insert calibrated pH probe, such as the Orion 8102BNV from Ross, into the solution. Measure the pH continuously. Adjust pH of Phenol Red/Deionized Water solution to 10.00+/−0.05 by adding 1 ml increments of Potassium Hydroxide/Deionized Water solution to the beaker containing the phenol red/deionized water solution while continually stirring.

C. Preparation of Antiperspirant Sample:

A film of the antiperspirant sample can be prepared using the following procedure. BYTAC TYPE VF-81 chemical resistant Norton FEP film is cut into 3×7 cm rectangles. A circle 2.2 cm in diameter is punched out. The protective back layer of the film is removed and the sticky side of the BYTAC film is adhered to a standard glass microscope slide. Care is taken such that the 2.2 cm circle cut out of the middle of the film is completely on the microscope slide. Antiperspirant is applied on the microscope slide in the center of the circle cut out of the BYTAC film. The antiperspirant sample is thoroughly spread throughout the circle by using a spatula or equivalent in a back and forth motion across the film surrounding the cut out circle. Spreading is continued until a smooth surface of antiperspirant product across the entire cut out circle is achieved. Carefully remove the BYTAC film from the microscope slide leaving behind the smooth, antiperspirant film. The antiperspirant film on the microscope slide is circular with a thickness equal to the thickness of the just removed BYTAC film (.about.0.1778 mm).

D. Application of pH Solution:

The antiperspirant film on the microscope slide is dried for 24 hours at ambient conditions (first drying period). After the first drying period, 20.0 microliters of the phenol red pH-indicator solution are applied to the center of the dried, antiperspirant sample using a standard micropipette such as the 5-50 microliter adjustable Finnpipette from Thermo Lab systems. The sample with the applied 20.0 microliters of phenol red ph indicator solution is left to dry for 24 hours at ambient conditions (second drying period).

E. Data Collection and Analysis:

During this second 24 hour drying period, the microscope slide with the dried antiperspirant film is placed face up on an approximate 15.24 cm×15.24 cm sample of black felt. A metal ring (1.8 cm diameter×2.5 cm height) is placed on the dried sample eliminating possible contamination of measurements by outside light sources. Care is taken to ensure the dried circle of phenol red ph solution is located in the center of the metal ring. A calibrated Minolta CR-300 series colorimeter, or equivalent, is placed on top of the metal ring. A standard spectral photometric measurement is taken and converted into standard L-a-b scale readings. At least four measurements are taken per sample. The average of the several (at least four) a-value readings is reported. Data can be collected at time points from 30 seconds after the phenol red indicator solution is added to up to 24 hours after the solution is added. This test is repeated three times with 3 samples per data time point and the results averaged to calculate color a-value.

Product Hardness

Antiperspirant soft solid compositions can be evaluated for product hardness (gram-force) and defined in terms of penetration force values. "Penetration force value" as used herein can represent a force required to move a standard 45° angle penetration cone through the composition for a distance of 10 mm at a rate of 2 mm/second. Values can be measured at 27° C. and 15% relative humidity using a TA-XT2 Texture Analyzer, available from Texture Technology Corporation, Scarsdale, N.Y., U.S.A. Higher values represent a harder product and lower values represent a softer product. The cone is available from Texture Technology Corp., as part number TA-15, and can have a total cone length of about 24.7 mm, an angled cone length of about 18.3 mm, and a maximum diameter of an angled surface of the cone of about 15.5 mm. The cone can have a smooth, stainless steel construction and weigh about 17.8 grams.

To operate the TA-XT2 Texture Analyzer, the cone, or probe, can first be attached to a probe carrier arm and cleaned with a low-lint wipe. Subsequently, a top stop and a bottom stop can be checked to ensure each is in a desired position. Test samples will generally be the composition inside the consumer applicator. Once samples have been properly prepared by removing any top portion of the container so that the cone or probe has access to the composition in the package, a product sample can be placed on a test base. A template can be used to ensure the product sample is at a desired location on the test base such that the cone can be in a position to contact the product sample at a midpoint between a canister side and a canister screw.

After the cone can be adjusted to about 1 cm above the product sample, a "RUN" button on the Texture Analyzer can be pressed. A measurement can be taken by the Texture Analyzer while a canister containing the product sample is held. The cone can take a measurement and automatically disengage from the product sample. Two measurements can be taken for each canister.

VII. Examples

| Ingredients | Inventive Solid Example 1 | Inventive Solid Example 2 | Inventive Soft Solid Example 1 |
|---|---|---|---|
| SF1202 Silicone Fluid | 27.91 | 27.73 | 62.25 |
| Aluminum Zirconium Trichlorohydrex Gly | 26.49 | | |
| Aluminum Zirconium Tetrachlorohydrex Gly | | 26.67 | 25.25 |
| Dow Corning 200 Fluid 10 Cst | | | 5.00 |
| Tribehenin | | | 2.00 |
| Synthetic Wax | | | 2.00 |
| PPG-14 Butyl ether | 6.50 | 6.50 | |
| C12-15 Alkyl Benzoate | 6.50 | 6.50 | |
| 556 Cosmetic Fluid | 3.00 | 3.00 | |
| Mineral Oil | 1.00 | 1.00 | |
| Petrolatum | 3.00 | 3.00 | |
| Stearyl Alcohol | 13.00 | 13.00 | |
| Castor Wax MP-80 | 2.9 | 2.9 | |
| Ozokerite | 1.00 | 1.00 | 1.00 |
| Behenyl Alcohol | 0.20 | 0.20 | |
| C20-40 Pareth 10 ethoxylate | 2.00 | 2.00 | 2.00 |
| Talc | 2.50 | 2.50 | |
| Cyclodextrin | 4.00 | 4.00 | 3.00 |
| | 100.00 | 100.00 | 100.00 |

Inventive Solid Examples 1 and 2 were prepared by a split stream process. In the hot stream tank, all of the waxes (stearyl alcohol, castor wax, ozokerite, behenyl alcohol), surfactant (C20-40 pareth 10 ethoxylate) and other emollients (C12-15 Alkyl benzoate, 556 Cosmetic fluid, petrolatum) and a lesser portion of the cylopentasilaxane are adding into one tank mixed and heated to 88° C. to melt the waxes. In the cold stream tank, all of the powders (active, talc, cyclodextrin), perfumes, PPG-14 butyl ether, and a greater portion of the cyclopentasiloxane are added and mixed and maintained at a temperature less than 50° C. Once each of the hot and cold streams are adequately mixed so they are homogenous, each of the process streams are simultaneously fed into a static mixer where they combine for about 5 seconds or less, to ensure a homogenous product while minimizing the mix time above the wax crystallization temperature. The product then exits the static mixer into individual canisters where it is allowed to cool to room temperature.

Inventive Soft Solid Example 1 was prepared by a split stream process. In the hot stream tank, all of the waxes (tribehenin, synthetic wax, ozokerite, behenyl alcohol), surfactant (C20-40 pareth 10 ethoxylate) and other emollients (dimethicone, petrolatum) and a lesser portion of the cylopentasilaxane are adding into one tank mixed and heated to 88° C. to melt the waxes. In the cold stream tank, all of the powders (active, cyclodextrin), perfumes, and a greater portion of the cyclopentasiloxane are added and mixed and maintained at a temperature less than 50° C. Once each of the hot and cold streams are adequately mixed so they are homogenous, each of the process streams are simultaneously fed into a static mixer where they combine for about 5 seconds or less, to ensure a homogenous product while minimizing the mix time above the wax crystallization temperature. The product then exits the static mixer into individual canisters where it is allowed to cool to room temperature.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A solid stick antiperspirant composition, comprising:
   an antiperspirant active selected from the group consisting of aluminum zirconium tetrachlorohydrex and aluminum zirconium trichlorohydrex, wherein the antiperspirant active has a concentration from 1% to about 35% by weight of the composition;
   one or more anhydrous liquid carriers;
   one or more structurants having a concentration from about 15% to about 25% by weight of the composition, wherein the one or more structurants comprises from about 10% to about 20%, by weight of the composition, of stearyl alcohol;
   a non-ionic ethoxylated linear alcohol having a carbon chain length from about 20 to about 40; and
   wherein the solid stick antiperspirant composition is a single phase.

2. The antiperspirant solid stick composition of claim 1, wherein the antiperspirant composition has a Red Dot Color Value of 0.4 or less at 2, 3, 4, 5, 10 and 15 minutes and a Red Dot Color Value greater than 1 at 30 seconds and a Red Dot Color Value of 1.25 or more at 24 hours.

3. The antiperspirant solid stick composition of claim 2, wherein the antiperspirant composition has a 24 hour diameter between about 2 and about 3.5 cm.

4. The antiperspirant solid stick composition of claim 1, wherein the non-ionic ethoxylated linear alcohol has an HLB value between about 6 and about 12.

5. The antiperspirant solid stick composition of claim 1, wherein the antiperspirant solid stick composition is anhydrous and has a hardness equal to or greater than 600 gram force.

6. The antiperspirant solid stick composition of claim 1, wherein the non-ionic ethoxylated linear alcohol has a concentration from about 1% to about 4% by weight of the antiperspirant composition.

7. The antiperspirant solid stick composition of claim 1, wherein at least one of the one or more structurants is selected from the group consisting of hydrogenated castor wax, ozokerite, behenyl alcohol, polyethylene, polymethylene, and a triglyceride.

8. The antiperspirant solid stick composition of claim 1, wherein the one or more anhydrous liquid carriers comprises a non-volatile silicone fluid.

9. The antiperspirant solid stick composition of claim 1, wherein the antiperspirant active is aluminum tetrachlorohydrex glycine.

10. An antiperspirant product, comprising a canister and the solid stick antiperspirant composition according to claim 1 disposed within the canister.

11. An antiperspirant solid stick composition, comprising:
    an antiperspirant active comprising a zirconium containing salt and having a concentration from about 1% to about 35% by weight of the composition;
    one or more anhydrous liquid carriers;
    one or more structurants having a concentration from about 15% to about 25% by weight of the composition, wherein the one or more structurants comprises from about 10% to about 20%, by weight of the composition, of stearyl alcohol;
    a non-ionic ethoxylated linear alcohol; and
    wherein the antiperspirant composition has a Red Dot Color Value of 0.5 or less at 2, 3, 4, 5, 10 and 15 minutes and a Red Dot Color Value greater than 1 at 30 seconds and a Red Dot Color Value of 1.25 or more at 24 hours.

12. The solid stick antiperspirant composition of claim 11, wherein the non-ionic ethoxylated linear alcohol has an HLB value between about 6 and about 12.

13. The solid stick antiperspirant composition of claim 11, wherein the non-ionic ethoxylated linear alcohol has a carbon chain length from about 20 to about 40.

14. The solid stick antiperspirant composition of claim 11, wherein the antiperspirant active further comprises glycine.

15. The solid stick antiperspirant composition of claim 11, wherein the antiperspirant active is aluminum zirconium trichlorohydrex or aluminum zirconium tetrachlorohydrex.

16. The solid stick antiperspirant composition of claim 11, wherein at least one of the one more structurants is selected from the group consisting of hydrogenated castor wax, ozokerite, behenyl alcohol, polyethylene, polymethylene, and a triglyceride.

17. The solid stick antiperspirant composition of claim 11, wherein the non-ionic ethoxylated linear alcohol has a concentration from about 1% to about 4% by weight of the antiperspirant composition.

18. A solid stick antiperspirant composition, comprising:
    an antiperspirant active comprising a zirconium containing salt and having a concentration from about 1% to about 35% by weight of the composition;
    one or more anhydrous liquid carriers;
    one or more structurants having a concentration from about 15% to about 25% by weight of the composition, wherein the one or more structurants comprises from about 10% to about 20%, by weight of the composition, of stearyl alcohol;
    a non-ionic ethoxylated linear alcohol having a carbon chain length from about 20 to about 40 and an HLB value between about 6 and about 12; and
    wherein the solid stick antiperspirant composition is a single phase.

19. The antiperspirant solid stick composition of claim 18, wherein the antiperspirant is aluminum zirconium tetrachlorohydrex or aluminum zirconium trichlorohydrex.

20. The antiperspirant solid stick composition of claim 18, wherein the antiperspirant composition has a Red Dot Color Value of 0.4 or less at 2, 3, 4, 5, 10 and 15 minutes and a Red Dot Color Value greater than 1 at 30 seconds and a Red Dot Color Value of 1.25 or more at 24 hours.

* * * * *